United States Patent [19]

Perkins

[11] Patent Number: 4,932,401
[45] Date of Patent: Jun. 12, 1990

[54] TWO-GAS VARIABLE RATIO, VARIABLE DOSE, METERING SYSTEM AND METHOD OF USE

[76] Inventor: Warren E. Perkins, 9960 S. A-1-A, Apt. 1901, Jensen Beach, Fla. 34957

[21] Appl. No.: 176,862

[22] Filed: Apr. 1, 1988

[51] Int. Cl.⁵ .......................................... A61M 15/00
[52] U.S. Cl. ........................... 128/203.12; 128/203.14; 128/204.23; 128/204.26; 128/205.18; 128/205.24
[58] Field of Search ....................... 128/204.18, 205.18, 128/203.12, 203.25, 204.21, 204.23, 204.26, 205.14, 205.24; 92/13.6, 103 R; 222/134, 250, 309; 264/313

[56] References Cited

U.S. PATENT DOCUMENTS

| | | | |
|---|---|---|---|
| 23,772 | 4/1859 | Marsh | 92/13.6 |
| 482,416 | 9/1892 | Siebert | 222/250 |
| 514,448 | 2/1894 | Desant | 128/205.18 |
| 1,213,302 | 1/1917 | Tullar | 128/205.18 |
| 1,241,056 | 9/1917 | Tullar | 128/205.18 |
| 1,266,624 | 5/1918 | Ramsay | 128/205.18 |
| 1,368,254 | 2/1921 | Habberley | 128/205.18 |
| 2,383,181 | 8/1945 | Enslin et al. | 128/205.18 |
| 2,770,231 | 11/1956 | Falk | 128/205.18 |
| 2,770,232 | 11/1956 | Falk | 128/205.18 |
| 3,137,215 | 6/1964 | Taplin | 92/103 R |
| 3,373,236 | 3/1968 | Taplin | 264/313 |
| 3,527,213 | 9/1970 | Schreiber | 128/203.25 |
| 3,734,092 | 5/1973 | Kipling | 128/203.25 |
| 3,737,073 | 6/1973 | Lupert | 222/134 |
| 3,788,313 | 1/1974 | Arp et al. | 128/145.8 |
| 4,054,133 | 10/1977 | Myers | 128/142.2 |
| 4,312,463 | 1/1982 | Daby | 222/134 |
| 4,381,002 | 4/1983 | Mon | 128/204.24 |
| 4,457,303 | 7/1984 | Durkan | 128/204.24 |
| 4,459,982 | 7/1984 | Fry | 128/205.14 |
| 4,554,916 | 11/1985 | Watt | 128/203.12 |
| 4,576,159 | 3/1986 | Hahn et al. | 128/203.25 |
| 4,621,747 | 11/1986 | van der Velde | 222/137 |
| 4,665,911 | 5/1987 | Williams et al. | 128/204.23 |
| 4,705,034 | 11/1987 | Perkins | 128/204.21 |
| 4,832,014 | 5/1989 | Perkins | 128/203.12 |

FOREIGN PATENT DOCUMENTS 87241  5/1921  Austria ........................... 128/205.18

Primary Examiner—Edgar S. Burr
Assistant Examiner—Aaron J. Lewis
Attorney, Agent, or Firm—Roland H. Shubert

[57] ABSTRACT

A displacement metering device for administering a mixture of oxygen and an anesthetic gas to a patient measures single dose quantities of each of the two gases in separate sets of gas displacing means and dispenses a dose of each gas in admixture to a patient during the inspiration phase of the patient's respiratory cycle. Co-ordinating means ensure that the two gases are delivered in constant ratio and also provide means for changing the ratio between the two gases. Means are also provided to change the volume, or dose size, of the two administered gases.

23 Claims, 2 Drawing Sheets

TWO-GAS VARIABLE RATIO, VARIABLE DOSE, METERING SYSTEM AND METHOD OF USE

BACKGROUND OF THE INVENTION

1. Field of the Invention

This invention relates to a means and method for administering two physiologically active gases, typically oxygen and an anesthetic, to a patient.

More particularly, this invention relates to a system for delivering variable doses of two gases at variable ratios of one gas to the other in response to a patient's breathing cycle and to a method for use of that system.

It is common to employ gases as anesthetics or analgesics in surgical procedures especially in dentistry. Gas administration devices used for this purpose typically provide a system for mixing oxygen with an anesthetic gas, usually nitrous oxide, and require two independent and continuous flow systems, one for each gas. The ratio of oxygen and anesthetic gas is varied during the procedure in order to control the level of sedation. It is of critical importance that an adequate level of oxygen be supplied to the patient with every breath and that the anesthetic gas be supplied only in admixture with oxygen else harm to the patient may well result.

The mixture of oxygen and anesthetic or analgesic gas is typically administered to the patient through a cannula or nasal mask as a continuously flowing stream. In a typical breathing cycle, the patient is inhaling for only about one-third of the time with the remainder of the cycle taken up by an exhalation and a pause after exhalation is complete. Thus, devices which continuously furnish oxygen and an anesthetic gas mixture result in wasting two thirds or more of the total gas supplied. While this wastage does have considerable economic significance, more importantly, there tends to result a buildup of physiologically active gases about the patient. Even with careful ventilation, there exists the danger that medical personnel attending the patient will be affected by the anesthetic. This hazard is particularly pronounced in dental surgery.

2. Description of the Prior Art

Applicant's prior U.S. Pat. No. 4,705,034 describes an inhalation responsive system for dispensing metered doses of two different gases. The system uses a pair of displacers, one for each gas, and includes means for varying the ratio of one gas to the other.

U.S. Pat. No. 4,457,303, to Durkan, discloses a respirator system for supplying supplemental oxygen to a patient which uses a fluidic laminar proportional amplifier to sense the start of an inspiration. Rate metered oxygen flow is started in response to the sensed inspiration and flow is continued for a time period shorter than the inspiration period.

Myers in U.S. Pat. No. 4,054,133 and Mon in U.S. Pat. No. 4,381,002 disclose devices which sense inhalation and exhalation pressure in the nasal cavity of a patient and convert those sensed pressures to signals which control the flow of oxygen to a patient.

None of the known prior art devices suggest a displacement type, inhalation responsive, two-gas variable ratio, variable dose, delivery system as described and claimed in this application.

SUMMARY OF THE INVENTION

A device for administering metered doses of oxygen and a second physiologically active gas to a patient in synchronization with the respiratory cycle and during the inspiration period of the patient utilizes two sets of displacer means, one for oxygen and the other for the second gas. Each displacer means set includes two piston and cylinder pairs with the pistons of each set connected so that they move in unison. Coordinating means between the two displacer means sets ensures that oxygen and the second gas are delivered at constant ratio during each dose and also allows that ratio to be changed. The dose sizes of both oxygen and the second gas are adjusted by varying the allowed piston strokes.

Hence, it is an object of this invention to provide a means and a method for delivering two gases in metered doses and in homogeneous admixture in response to a patient's breathing cycle with provision for adjustments of both the gas doses and the ratio of one gas dose to the other.

It is another object of this invention to provide means for the administration of oxygen with an anesthetic or analgesic gas in adjustable ratio and amount while minimizing the contamination of the local atmosphere with the anesthetic gas.

Other objects of the invention will be apparent from the following description of certain preferred embodiments of the invention.

DESCRIPTION OF THE DRAWING

Specific embodiments of the invention are illustrated in the drawing in which:

FIG. 3 illustrates a rolling diaphram type of piston displacing means useful in certain embodiments of this invention.

DESCRIPTION AND DISCUSSION OF THE INVENTION

Figure 1:
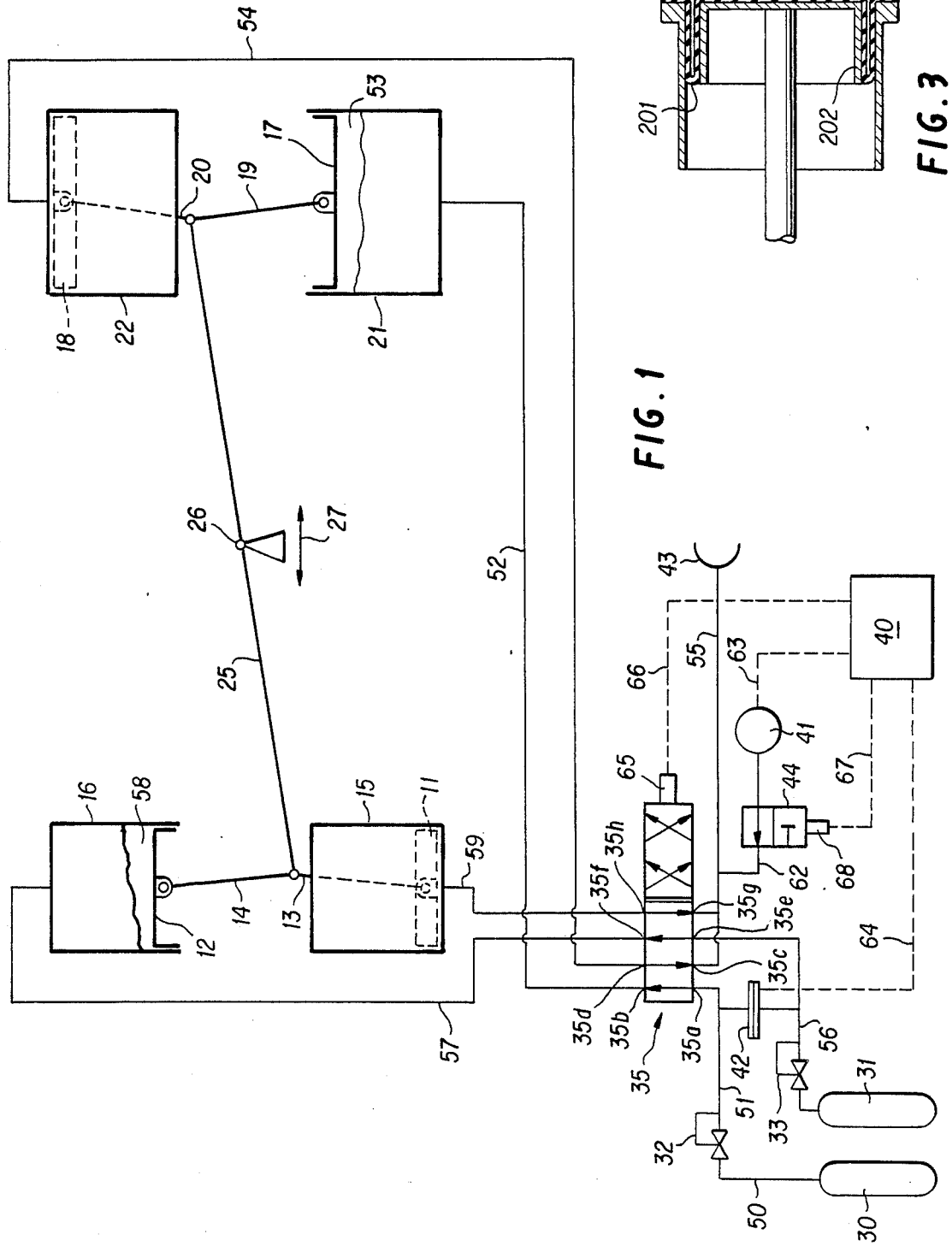
FIG. 1 is generally schematic depiction of the gas circuitry and control system of this invention.

Various embodiments of this invention will be described and discussed in detail with reference to the drawing figures.

Referring now to FIG. 1, there is shown in generally schematic form the system, including the gas circuitry and controls, for delivering two gases in response to a patient's breathing cycle. The system comprises two pairs of gas metering and delivery displacers, which may be either of the piston or bellows type, arranged to operate synchronously. The first displacer pair preferably comprises two piston, 11 and 12, connected through piston rods 13 and 14, and arranged to reciprocate within mating cylinders 15 and 16. Likewise, the second displacer pair includes two pistons, 17 and 18, connected through piston rods 19 and 20, and arranged to reciprocate back and forth in cylinders 21 and 22. Movement of the piston pairs is synchronized and controlled by action of coordinating lever 25. One end of lever 25 is pivotally attached to the ends of piston rods 13 and 14 while the other lever end is similarly attached to the ends of piston rods 19 and 20. Lever 25 pivots about a point 26 intermediate its ends. Point 26 is arranged to move along lever 25, as shown by arrow 27, thereby allowing the ratio of travel of the first piston pair to the second piston pair to be adjusted or varied.

There is also provided a source of oxygen which suitably may be pressure tank 30. A source of a second physiologically active gas having anesthetic or analgesic properties, hereafter referred to generally as an anesthetic gas, likewise may be a pressure tank 31. Gas pressure regulators 32 and 33 ensure that oxygen and the anesthetic gas are supplied at essentially fixed regulated pressures to a valve means 35 which routes gas flow to and from the two pairs of displacer pistons. As depicted in the drawing, valve 35 is an 8-way, two position valve but it may be as well a plurality of ganged valves. The movement of valve 35 between its first position and its second position is governed by controller means 40 which, in turn, responds to signals produced by sensor means 41 and differential pressure switch 42 in a manner which will later be described. Controller 40 is also arranged to alternately connect sensor 40 with, and isolate it from, cannula 43 by operation of valve means 44.

The system of this invention supplies metered and proportioned doses of oxygen and of an anesthetic gas to a patient in response to and in synchronization with the patient's respiratory cycle. Operation of the device will be more clearly understood by following it through one complete respiratory cycle. When the device is in use, cannula 43 is inserted into the nostrils of the patient; it being understood that a mask or similar device can be substituted for the cannula. Assume that, in the system mode shown, the patient has completed an exhalation but has not yet begun an inhalation. Tracing first the path taken by oxygen through the system, oxygen from high pressure source 30 is conveyed by way of line 50 through pressure regulator 32 and thence to valve port 35a via line 51. In the valve position shown, port 35a connects to port 35b allowing oxygen to flow to cylinder 21 by way of line 52. The force of the incoming oxygen gas pushes piston 17 upwardly in the bore of cylinder 21 until piston 18, to which it is connected, reaches the end of its travel in mating cylinder 22. Because there is open communication between pressure regulator 32 and the interior volume 53 of cylinder 21, it can be appreciated that the gas pressure in cylinder 21 is at regulator pressure. It can also be appreciated that the interior volume 53 is set by the limit of travel of piston 18. Because the oxygen pressure and the interior volume 53 are both fixed and known, the quantity of oxygen now contained within cylinder 21 is also fixed and known. That quantity is the unit dose delivered to a patient upon an inhalation.

Conduit 54 communicates between the interior of cylinder 22 and valve port 35d. Oxygen which had been contained in cylinder 22 was pushed out of the cylinder by movement of piston 18 under the force of incoming oxygen on piston 17. Valve port 35d is connected to valve port 35c which allows oxygen to flow from conduit 54, through the valve, and thence to cannula 43 by way of conduit 55.

Tracing next the path taken by the anesthetic gas through the system, an anesthetic gas at a relatively high pressure is supplied by source 31 to pressure regulator 33. Regulator 33 is set to provide a constant or known down stream pressure in conduit 56. Conduit 56 terminates at valve port 35e which in turn connects to port 35f. Line 57 provides communication between the interior of cylinder 16 and valve port 35f. In the valve position shown, the pressure within the interior volume 58 of cylinder 16 is equal to the pressure in conduit 56. Because piston 11 is at the limit of its travel in cylinder 15, the volume 58 is at its maximum and this volume defines a unit dose of anesthetic gas delivered to a patient upon a single inhalation.

Conduit 59 communicates between the interior of cylinder 15 and valve port 35h. Port 35h connects to port 35g which, in turn, connects to line 55 leading to cannula 43. Anesthetic gas which had been contained in cylinder 15 was Pushed from the cylinder into conduit 59 by piston 11 moving under the force of the incoming gas on piston 12 to which it is connected. Both piston pairs are required to act in concert by their interconnection through coordinating lever 25. Hence, the anesthetic gas contained in cylinder 15 and the oxygen contained in cylinder 22 are simultaneously discharged at the selected ratio of flow rates into conduit 55 where they mix and flow together for breathing by the patient.

Presume now that the patient begins an inhalation. That act causes a slight pressure drop or flow in line 55. A sensor 41 is in communication with line 55 through line 61, open valve 44 and branch line 62. It is required that sensor 41 be of a type which responds very rapidly to those slight pressure changes or flows indicative of the onset of an inhalation of the patient. Exemplary sensors meeting those requirements and known in the prior art include a spring-loaded diaphragm sensor as shown by Myers in U.S. Pat. No. 4,054,133 and fluidic devices employing laminar proportional amplifiers as shown by Mon in U.S. Pat. No 4,381,002 and Durkan in U.S Pat. No. 4,457,303. Other types of detectors, including sensitive pressure-to-electric switches and those sensing gas flow using thermistors, may be used as well.

Upon sensing the onset of an inhalation, sensor 41 produces a signal, which may be electrical or pneumatic, and transmits that signal via means 63 to controller 40. Differential pressure switch 42 is arranged to transmit a blocking signal 64 to controller 40, which prevents operation of the system, in the event that the pressure in conduits 51 and 56 are not at the set pressures of the regulators. The two regulators, 32 and 33, may be set at the same or at different pressures. Monitoring of the differential pressure between conduits 51 and 56 by switch 42 assures that both gas supply systems are functioning thereby preventing administration of only one of &he gases. The differential pressure switch also prevents release of the doses of oxygen and anesthetic gas to the patient before the filling of both cylinder chambers is complete thus ensuring that the two gases are delivered in the proper ratio.

Controller 40 upon receiving a signal from sensor 41, and in the absence of a blocking signal from differential pressure switch 42, transmits a signal to valve actuator 65 by way of transmission means 66 whereby valve 35 is caused to move to its second position. At that same time, a second signal is transmitted by way of means 67 to valve actuator 68 causing valve 44 to move to its other position thus blocking communication between sensor 41 and gas delivery line 55. In this way, the sensor 40 is shielded from the rush of gas released from interior volume 58 of cylinder 16 and interior volume 53 of cylinder 21 into line 55 leading to the cannula. Controller 40 includes means such as an interval timer to maintain valve 44 in its closed position for a period of time, typically about half a second, to allow the pressure in line 55 to return to normal. At the end of that timed interval, controller 40 de-energizes valve activator 68 causing valve 44 to return to its open position re-connecting sensor 41 with line 55 through line 62.

When valve 35 is in its second position, the flow of gas through the valve is diagrammed by the arrows on the right half of the valve. Thus, in the second valve position, port 35a connects to port 35d; port 35b to port 35c; port 35e to port 35h; and port 35f to port 35g. Oxygen is thus routed through the valve into line 54 and thence to the interior of cylinder 22 while the oxygen contained within the interior volume of cylinder 21 is conducted to cannula 43 via lines 52 and 55. Similarly, the anesthetic gas is routed through the valve into line 59 and thence to the interior of cylinder 15 while the gas contained in cylinder 16 merges with the oxygen flow to the cannula. At the same time, incoming pressurized oxygen is pushing on piston 18 while pressurized anesthetic gas is similarly pushing on piston 11 to move the piston pairs to their limiting positions and to expel the premeasured doses of oxygen and anesthetic gases.

The patient's subsequent inhalation is detected by sensor 41 triggering controller 40 to cycle valve 35 to its first position thus starting a new cycle which is repeated over and over as the patient breathes.

As can now be appreciated, the interconnection of the two cylinder-piston pairs by means of the coordinating lever 25 maintains the expulsion rate of oxygen relative to that of the anesthetic gas at a constant value. The ratio of oxygen to anesthetic gas delivered during each cycle may be adjusted by moving the pivot point 26 of lever 25. Dose size, or the amount of oxygen and of anesthetic gas delivered per cycle, is also adjustable by changing the stroke of the pistons within their respective cylinders. A mechanical system for accomplishing these results is shown in FIG. 2.

Figure 2:
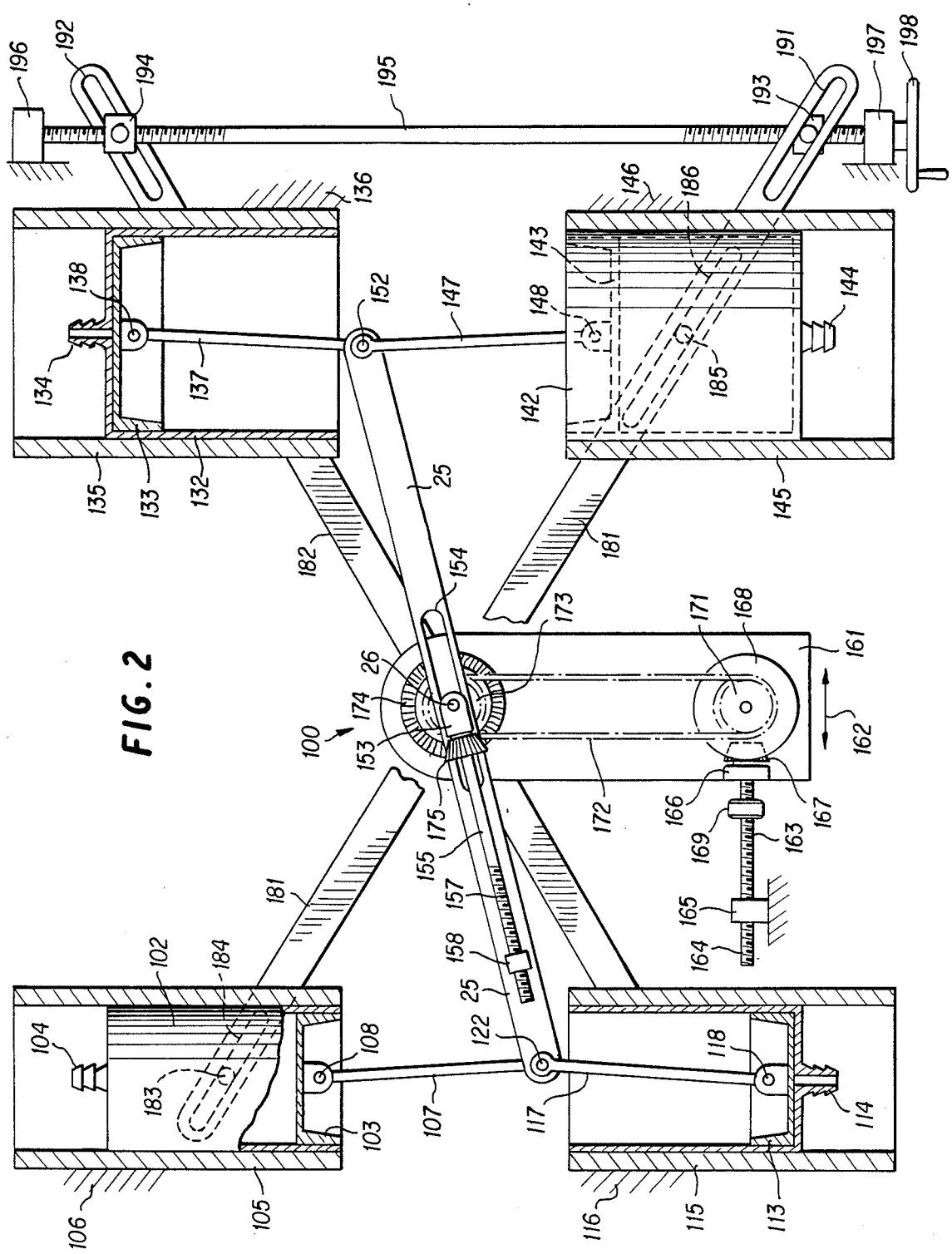
FIG. 2 depicts in partial section a preferred mechanical arrangement of the two-gas variable displacement, variable ratio system of this invention.

Referring now to FIG. 2, there is shown generally at 100 a variable displacement, variable ratio, two-gas metering system in accordance with this invention. The system includes two sets of gas displacement means which in a preferred embodiment comprise two piston and cylinder pairs for each of the two sets. The first piston-cylinder pair comprises a cylinder 102 having an open end into which a piston 103 is fitted. The other end of cylinder 102 is closed except for the provision of a gas inlet-outlet port 104 adapted for connection to a gas conduit (not shown). Cylinder 102 is mounted within sleeve 105 which is arranged to allow axial movement of the cylinder within the sleeve but to restrain the cylinder from all other movement.

The other member of the first piston-cylinder pair includes a cylinder 112 with mating piston 113 and having a port 114 at its closed end for connection to a gas conduit. Piston 113 is of the same diameter as is piston 103. Cylinder 112 is mounted in sleeve 115 which allows axial movement of the cylinder within the sleeve. Sleeves 105 and 115 are rigidly secured in axial alignment one to the other by connection to a frame or housing (not shown) by means of attachments 106 and 116 respectively. A piston rod 107 is attached to piston 103 by means of wrist pin 108. Similarly, piston rod 117 attaches to piston 113 through wrist pin 118. The other ends of piston rods 107 and 117 commonly connect to an end of coordinating lever 25 through pin 122. Coordinating lever 25, in turn, is pivoted intermediate its ends on pivot shaft 26. As can be seen by that arrangement, the travel of pistons 103 and 113 is tied together by the piston rods such that when one chamber or cylinder volume is increasing, the other is decreasing.

The second piston-cylinder set, which is for oxygen, is similar to the first except that the diameter of the pistons will ordinarily be somewhat larger than that of the first set because the dose of oxygen administered to a patient per breath usually is larger than is the dose of anesthetic gas. A piston 133 is fitted to move within cylinder 132 which has a port 134 for connection to a gas conduit. Cylinder 132 is mounted for axial movement within sleeve 135 which is attached through means 136 to the frame or housing.

The other member of the second piston-cylinder pair consists of a piston 143 movable within cylinder 142. Piston 143 is axially aligned with piston 133. Cylinder 142 is provided with a gas port 144 and is arranged for axial movement within sleeve 145. Sleeve 145, in turn, is fixed to the frame by a weldment or other attachment at 146. A piston rod 137 is attached to piston 132 through wrist pin 138. Similarly, piston rod 147 attaches to piston 143 through wrist pin 148. The other ends of piston rods 137 and 147 are connected through pin means 152 to the other end of coordinating lever 25 causing the pistons 133 and 143 to move in tandem.

Because each end of coordinating lever 25 is tied to a piston pair through their respective piston rods, it can be appreciated that the ratio of travel of the two sets of pistons is proportional to the position of pivot shaft 26 along the length of coordinating lever 25. Lever 25 is provided with a variable pivot point to allow changing of the ratio of travel of the oxygen and anesthetic gas displacing piston pairs. Adjustment of the pivot point is accomplished by providing a yoke 153 which fits over the pivot shaft 26 and is movable back and forth within slot 154 of lever 25. An adjustment shaft 155 connects at one end to yoke 153. Threading 157, which engages threaded nut 158 attached to lever 25, is provided at the other end of shaft 155. Rotation of the adjustment shaft causes pivot shaft 26 to move relative to coordinating lever 25 along slot 154.

As has been set out previously, the two set; of cylinder-piston pairs are fixed relative to each other. Consequently, the ends of coordinating lever 25 must be maintained in a constant position relative to the piston, cylinder and sleeve assemblies throughout the range of adjustment of the pivot shaft 26 along the coordinating lever. This is done by providing a pivot shaft mounting block 161 which is movable back and forth along line 162 between the two sets of piston-cylinder pairs. Movement of the mounting block 161 is effected by providing a positioning shaft 163 having a threaded end 164 engaging a threaded nut 165 which is fixed to the frame by attachment means 166. Turning adjustment nut 169 causes shaft 163 to rotate and to act through collar 166 causing movement of mounting block 161. At the same time the rotary motion of shaft 163 is transmitted to a first set of bevel gears 167 and 168, then through a sprocket 171 and chain 172 to a second sprocket 173 and thence to a second set of bevel gears 174 and 175. Bevel gear 175 is fixed to adjustment shaft 155 causing it to turn when positioning shaft 163 is turned. The net effect, then, is that the pivot shaft 26 moves relative to the frame of the device but the coordinating lever 25 does not. The piston stroke and hence the volume of the gas pulse delivered by each of the pistons moving in its respective cylinder is adjusted by moving the cylinders axially within their sleeves either closer together or further apart. The axial position of the cylinders within their respective sleeves is controlled by a pair of cylinder position locating levers 181 and 182. Each of levers 181 and 182 are rotatably mounted on pivot shaft 26 at a point intermediate the lever ends. Lever 181 connects diagonally opposite cylinders 102 and 142 through a pin and slot arrangement. There is provided a pin 183 extending outwardly from the side of cylinder 102 and slidably fitting within a slot 184 provided at a location near the end of lever 181. Similarly, pin 185 extends outwardly from the side of cylinder 142 and slides within slot 186 formed toward the other end of lever 181. Diagonally opposite cylinders 112 and 132 are likewise connected through an identical pin and slot arrangement (not shown) to lever 182.

Adjustment of the cylinder spacing, and hence the piston stroke, is accomplished by providing slots 191 and 192 near the extreme ends of levers 181 and 182 respectively. A traveling block-pin assembly 193 thread mounted to cylinder positioning shaft 195, is arranged to mesh with slot 191 of lever 181. Likewise, a traveling block-pin assembly 194 is thread mounted near the other end of positioning shaft 195 and arranged to mesh with slot 192 of lever 182. Shaft 195 is axially secured by collars 196 and 197 located adjacent the shaft ends. That portion of shaft 195 to which traveling block 193 is mounted is threaded opposite to that of the shaft portion to which traveling block 194 is mounted. Thus, rotation of shaft 195 by turning adjustment wheel 198 causes the two traveling blocks to move in opposite directions which in turn moves the cylinders in each of the two piston-cylinder pairs either closer together or farther apart. No matter what the adjustment of either the cylinder volumes, by movement of the cylinder position locating levers, or the ratio of piston stroke by movement of the coordinating lever relative to its pivot point, the pistons always travel to their cylinder ends. Thus, a complete displacement of the gas charge within each cylinder is accomplished o each piston stroke regardless of either displacement or ratio whereby the accuracy of dose volume delivery is optimized.

FIG. 3 represents one preferred embodiment of a piston-cylinder combination useful in this invention. The illustrated device is commercially available under the tradename Bellofram Rolling Diaphram and is described in detail in U.S. Pat. Nos. 3,137,215 and 3,373,236. As shown in FIG. 3, the device includes a diaphram 201 which is formed in the shape of a truncated cone with its center fastened to the head of piston 202 and its outer flange clamped to cylinder 203. Diaphram 201 alternately rolls and unrolls on the skirt of piston 202 and the wall of cylinder 203 as the piston travels back and forth. The rolling action of the diaphram eliminates sliding contact and breakaway friction and forms a complete seal preventing blow-by leakage and pressure loss. These attributes, coupled with the fact that the device requires no lubrication of any kind, makes it especially attractive as a component in the device of this invention.

While this invention has been described in terms of certain preferred embodiments, it will be understood that a variety of functional an mechanical equivalents to those elements making up the inventive device will be obvious to those skilled in the art and that substitution of such equivalents is within the spirit and scope of the appended claims.

I claim:

1. A device for administering pulsed doses of oxygen and an anesthetic gas to a patient in synchronization with the patient's breathing cycle comprising:
   two sets of gas displacer means, the first set for oxygen and the second set for the anesthetic gas, each set of said displacer means comprising two piston and cylinder pairs, each of said piston-cylinder pairs comprising a piston arranged to reciprocate within a cylinder, each said cylinder having one closed end, each said closed end having a single port for connection to a gas conduit, the two pistons in each said set connected so as to move in unison;
   lever means connecting the pistons of the two gas displacer means sets and arranged to synchronize the movement of the pistons of one said set with the movement of the pistons of the other said set;
   means to cause the pistons of each said gas displacer set to move in response to and in synchronization with the breathing cycle of a patient, and
   means for adjusting the length of stroke of said pistons moving in their respective cylinders, said means arranged to cause each of said pistons of both said gas displacer means to travel to its respective cylinder end on each piston stroke to thereby completely displace the gas charge within each said cylinder.

2. The device of claim 1 wherein each cylinder is mounted in a sleeve, said sleeve allowing its contained cylinder to move only in an axial direction.

3. The device of claim 2 wherein said means for adjusting the stroke of said pistons comprises means for moving the cylinders of each gas displacer set within their respective sleeves toward or away from each other.

4. The device of claim 3 wherein said cylinder moving means comprises a pair of cylinder position locating levers, each of said levers connecting a cylinder of said first set with a diagonally opposite cylinder of said second set, each said levers pivoted at a point intermediate its ends about a common shaft.

5. The device of claim 4 wherein said common shaft is mounted on a block, said block adjustably movable along a line between said first and second gas displacer means.

6. The device of claim 5 wherein said lever means connecting the pistons of the two gas displacer sets is also pivoted about said common shaft at a point intermediate its ends.

7. The device of claim 4 wherein said cylinders are connected to said position locating levers by means of pins extending outwardly from the cylinder sides and adapted to slidably fit within slots provided in said levers.

8. The device of claim 7 including means for moving the ends of said cylinder position locating levers either closer together or further apart thereby causing adjustment of the position of said cylinders within their respective sleeves.

9. A system for administering pulsed doses of gaseous oxygen and an anesthetic gas to a patient in synchronization with the respiratory cycle of the patient and during the inhalation phase of said cycle, comprising:
   a set of oxygen displacers and a set of anesthetic gas displacers, each set having two gas displacement means arranged to operate in unison;
   means to synchronize the operation of the set of oxygen displacers with the operation of the set of anesthetic gas displacers;
   valve means adapted to move back and forth between a first position and a second position in response to sensed inhalations of the patient;
   first conduit means arranged when said valve means is in its first position to connect a source of oxygen through said valve means to one of said oxygen gas displacement means and to connect the other of said oxygen gas displacement means through said valve means to a cannula adapted to communicate with the nasal passages of the patient and to reverse said connections when the valve means is in its second position; and second conduit means arranged when said valve means is in its first position to connect a source of anesthetic gas through said valve means to one of said anesthetic gas displacement means and to connect the other of said anesthetic gas displacement means through said valve means to said cannula and to reverse said connections when the valve means is in its second position.

10. The system of claim 9 including sensor means responsive to the onset of an inhalation of the patient and adapted to cause a signal to be transmitted to valve activating means in response to said inhalation onset whereby said activating means cause said valve means to move from one of its positions to the other of its positions.

11. The system of claim 10 including means to isolate said sensor means from the rest of the system for a short period of time after transmission of a signal to said valve activating means.

12. The system of claim 10 including means for supplying oxygen to said set of oxygen displacers at an essentially fixed pressure and means to supply said anesthetic gas to said set of anesthetic gas displacers at a fixed pressure.

13. The system of claim 12 including means to measure the differential pressure between said supplied oxygen and anesthetic gas, said means adapted to produce a signal which will prevent operation of said valve activating means if the pressures of the two gases are not at the desired levels.

14. The system of claim 13 wherein each said gas displacement means comprises a piston and cylinder pair, said piston arranged to reciprocate within said cylinder, each said cylinder having one closed end and having a port for connection to a gas conduit, the two pistons in each said set connected so as to move in unison.

15. The system of claim 14 wherein said means to synchronize the operation of said oxygen and anesthetic gas displacement means comprises a lever means connecting the pistons of the two sets, said lever means pivoted about a shaft intermediate its ends.

16. The system of claim 15 wherein the cylinder of each said piston and cylinder pair is mounted in a sleeve, said sleeve allowing its contained cylinder to move only in an axial direction.

17. The system of claim 16 including means for adjusting the stroke of said pistons moving in their respective cylinders, said adjusting means comprising means for moving the cylinders of each gas displacement means set within their respective sleeves either toward or away from each other.

18. The system of claim 17 wherein said cylinder moving means comprises a pair of cylinder position locating levers, each of said levers connecting a cylinder of said oxygen displacer set with a diagonally opposite cylinder of said anesthetic gas displacer set, each said levers pivoted intermediate its ends about said shaft.

19. The system of claim 18 wherein said shaft is mounted on a block, said block adjustably movable along a line between the two sets of gas displacers.

20. The system of claim 19 wherein said cylinders are connected to said position locating levers by means of pins extending outwardly from the cylinder sides and adapted to slidably fit within slots provided in said levers.

21. A method for administering one pair of adjustably premetered doses of physiologically active respiratory gases in synchronism with the breathing cycle of a patient while simultaneously premetering a second, equal set of the same two gases in preparation for the next dose delivery comprising:

volumetrically premetering and storing at constant pressure a first adjustable dose of a first physiologically active gas into a first gas displacer means while simultaneously volumetrically premetering and storing at constant pressure a second dose of a second physiologically active gas into a second gas displacer means in adjustably coordinated ratio to the said first dose; and in response to a signal triggered by the onset of an inhalation of said patient, delivering by forced displacement both of said doses to said patient at the same volumetric ratio of flow rates as the ratio of the premetered volumes while simultaneously volumetrically premetering another set of equally sized doses of both gases into said first and second displacer means, and repeating the cycle of simultaneous premetering and delivery actions in response to subsequent signals signifying the onset of subsequent inhalations.

22. The method of claim 21 wherein said first physiologically active gas is oxygen and the second physiologically active gas is an anesthetic.

23. The method of claim 22 wherein said second gas is nitrous oxide.

* * * * *